(12) United States Patent
Martin et al.

(10) Patent No.: US 7,781,224 B2
(45) Date of Patent: Aug. 24, 2010

(54) SAFE BIODEGRADABLE FLUORESCENT PARTICLES

(75) Inventors: Sue I. Martin, Berkeley, CA (US); David P. Fergenson, Alamo, CA (US); Abneesh Srivastava, Santa Clara, CA (US); Michael J. Bogan, Dublin, CA (US); Vincent J. Riot, Oakland, CA (US); Matthias Frank, Oakland, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 1033 days.

(21) Appl. No.: 11/502,301

(22) Filed: Aug. 9, 2006

(65) Prior Publication Data

US 2009/0221087 A1   Sep. 3, 2009

Related U.S. Application Data

(60) Provisional application No. 60/707,520, filed on Aug. 10, 2005.

(51) Int. Cl.
   *G01N 21/76* (2006.01)
(52) U.S. Cl. ...................................... 436/172
(58) Field of Classification Search .................. 436/172
   See application file for complete search history.

(56) References Cited

U.S. PATENT DOCUMENTS

| | | | |
|---|---|---|---|
| 4,623,588 A * | 11/1986 | Nuwayser et al. ...... 428/402.24 |
| 5,827,531 A * | 10/1998 | Morrison et al. ............ 424/450 |
| 6,287,542 B1 * | 9/2001 | Bernard et al. ................. 424/49 |
| 6,498,041 B1 | 12/2002 | Tabacco et al. | |
| 6,532,067 B1 | 3/2003 | Chang et al. | |
| 6,632,526 B1 | 10/2003 | Chandler et al. | |
| 6,859,570 B2 | 2/2005 | Walt et al. | |
| 7,056,517 B2 * | 6/2006 | Smith et al. .............. 424/190.1 |
| 2003/0138875 A1 * | 7/2003 | Powers et al. ................. 435/34 |
| 2003/0223063 A1 | 12/2003 | Hill et al. | |
| 2004/0125371 A1 | 7/2004 | Chang et al. | |
| 2004/0258759 A1 * | 12/2004 | Suslick et al. ................ 424/490 |
| 2005/0048121 A1 * | 3/2005 | East et al. .................... 424/486 |

OTHER PUBLICATIONS

Venkatram, A., "An examination of the urban dispersion curves derived from the St. Louis dispersion stury," Atmospheric Environment 39 (2005) 3813-3822.
Langlois, R., "Detecting Bioaerosols When Time Is of the Essence," Lawrence Livermore National Laboratory, Science & Technology Review, Oct. 2004, 2 pages.
Yuan, J., et al., "Dispersion within a model urban area," Atmospheric Environment 39 (2005) 4729-4743.

(Continued)

*Primary Examiner*—Lore Jarrett
(74) *Attorney, Agent, or Firm*—Eddie E. Scott; John H. Lee (57) ABSTRACT

A human-safe fluorescence particle that can be used for fluorescence detection instruments or act as a safe simulant for mimicking the fluorescence properties of microorganisms. The particle comprises a non-biological carrier and natural fluorophores encapsulated in the non-biological carrier. By doping biodegradable-polymer drug delivery microspheres with natural or synthetic fluorophores, the desired fluorescence can be attained or biological organisms can be simulated without the associated risks and logistical difficulties of live microorganisms.

17 Claims, 4 Drawing Sheets

OTHER PUBLICATIONS

Ho, J., et al., "Estimating aerosol hazards from an anthrax letter," Aerosol Science 36 (2005) 701-719.

Lai, A., "Investigation of Electrostatic Forces on Particle Deposition in a Test Chamber," Indoor and Built Environment, 15; 2, 2006, 179-186.

Sexto, R.G., "Modeling the Spread of Anthrax in Buildings," Indoor Air, Lawrence Berkeley National Lab, 2002, 506-511.

Langlois, R., "Rapid Field Detection of Biological Agents," Science & Technology Review, Lawrence Livermore National Lab, Jan./Feb. 2002, 6 pages.

Chang, J., et al., "Use of Salt Lake City URBAN 2000 Field Data to Evaluate the Urban Hazard prediction Assessment Capability 9HPAC) Dispersion Model," American -Cont'd. Meteoroligical Society, Apr. 2005, 485-501.

\* cited by examiner

SAFE BIODEGRADABLE FLUORESCENT PARTICLES

CROSS-REFERENCE TO RELATED APPLICATIONS

This application claims the benefit of U.S. Provisional Patent Application No. 60/707,520 filed Aug. 10, 2005 and titled "Doped Spheres of Biodegradable Polymers as Fluorescence Simulants." U.S. Provisional Patent Application No. 60/707,520 filed Aug. 10, 2005 and titled "Doped Spheres of Biodegradable Polymers as Fluorescence Simulants" is incorporated herein by this reference.

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to particles and more particularly to a safe fluorescent particle.

2. State of Technology

The article "An examination of the urban dispersion curves derived from the St. Louis dispersion study" by Akula Venkatram in *Atmospheric Environment* 39 (2005) 3813-3822, describes an aerosol study that was conducted over the period 1963-1965. The aerosol study was an investigation of large scale air dispersal to track particulate migration over vast areas, or for urban particle dispersion studies. Researchers performing these studies rely on air dispersion models and gas tracer tests to determine the movement and flow of aerosols in urban environments such as in cities—around and through occupied buildings—because "safe" particles were not available at the time. The St. Louis study consisted of a series of 26 daytime and 16 evening experiments in which fluorescent zinc cadmium sulfide particles were released near ground level at two different locations under a variety of meteorological conditions. During the first year of the experiments, the release was at ground level in a relatively open area in a park located west of the downtown area. In the second year, the tracer was released from the top of a three-story building surrounded by trees and similar buildings. The main downtown area, consisting of buildings with an average height of 40 m, was about 5 km away from both release locations.

In an article titled, "U.S. Is Deploying a Monitor System for Germ Attacks," by Judith Miller in The New York Times on Jan. 22, 2003, it was reported, "To help protect against the threat of bioterrorism, the Bush administration on Wednesday will start deploying a national system of environmental monitors that is intended to tell within 24 hours whether anthrax, smallpox and other deadly germs have been released into the air, senior administration officials said today. The system uses advanced data analysis that officials said had been quietly adapted since the September 11 attacks and tested over the past nine months. It will adapt many of the Environmental Protection Agency's 3,000 air quality monitoring stations throughout the country to register unusual quantities of a wide range of pathogens that cause diseases that incapacitate and kill . . . The new environmental surveillance system uses monitoring technology and methods developed in part by the Department of Energy's national laboratories. Samples of DNA are analyzed using polymerase chain reaction techniques, which examine the genetic signatures of the organisms in a sample, and make rapid and accurate evaluations of that organism . . . . Officials who helped develop the system said that tests performed at Dugway Proving Ground in Utah and national laboratories showed that the system would almost certainly detect the deliberate release of several of the most dangerous pathogens. 'Obviously, the larger the release, the greater the probability that the agent will be detected,' an official said. 'But given the coverage provided by the E.P.A. system, even a small release, depending on which way the wind was blowing and other meteorological conditions, is likely to be picked up.'"

In an article titled, "Biodetectors Evolving, Monitoring U.S. Cities," by Sally Cole in the May 2003 issue of Homeland Security Solutions, it was reported, "The anthrax letter attacks of 2001, and subsequent deaths of five people, brought home the reality of bioterrorism to Americans and provided a wake-up call for the U.S. government about the need for a method to detect and mitigate the impact of any such future attacks. Long before the anthrax letter attacks, scientists at two of the U.S. Department of Energy's national laboratories, Lawrence Livermore National Laboratory (LLNL) and Los Alamos National Laboratory (LANL), were busy pioneering a "biodetector" akin to a smoke detector to rapidly detect the criminal use of biological agents. This technology is now expected to play a large role in the U.S. government's recently unveiled homeland security counter-terrorism initiative, Bio-Watch, which is designed to detect airborne bioterrorist attacks on major U.S. cities within hours. Announced back in January, Bio-Watch is a multi-faceted, multi-agency program that involves the U.S. Department of Energy, the Environmental Protection Agency (EPA), and the U.S. Department of Health and Human Services' Centers for Disease Control and Prevention (CDC). Many of the EPA's 3,000 air-quality monitoring stations throughout the country are being adapted with biodetectors to register unusual quantities of a wide range of pathogens that cause diseases that incapacitate and kill, according to the EPA. The nationwide network of environmental monitors and biodetectors, which reportedly will eventually monitor more than 120 U.S. cities, is expected to detect and report a biological attack within 24 hours. Citing security reasons, the EPA declined to disclose further details about the program at this time . . . . The Autonomous Pathogen Detection System (APDS) is a file-cabinet-sized machine that sucks in air, runs tests, and reports the results itself. APDS integrates a flow cytometer and real-time PCR detector with sample collection, sample preparation, and fluidics to provide a compact, autonomously operating instrument capable of simultaneously detecting multiple pathogens and/or toxins. The system is designed for fixed locations, says Langlois, where it continuously monitors air samples and automatically reports the presence of specific biological agents. APDS is targeted for domestic applications in which the public is at high risk of exposure to covert releases of bioagents—subway systems, transportation terminals, large office complexes, and convention centers . . . . APDS provides the ability to measure up to 100 different agents and controls in a single sample; Langlois says. 'It's being used in public buildings right now.' The latest evolution of the biodetector, APDS-II, uses bead-capture immunoassays and a compact flow cytometer for the simultaneous identification of multiple biological simulants. Laboratory tests have demonstrated the fully autonomous operation of APDS-II for as long as 24 hours."

U.S. Pat. No. 6,498,041 issued Dec. 24, 2002 to Mary Beth Tabacco and Laura C. Taylor for optical sensors for rapid, sensitive detection provides the following state of technology information: "The threat from biological weapons as tools of modern warfare and urban terrorism is increasing. Development of early detection, counter measures, and remediation technology is a high priority in many military, government and private laboratories around the world. Biological warfare (BW) agents of critical concern are bacterial spores, such as *Bacillus anthracis* (anthrax), *Clostridium tetani* (tetanus), and *Clostridium botulinum* (botulism)."

United States Published Patent Application No. 2004/0125371 by Richard Chang et al published Jul. 1, 2004 for method and instrumentation for measuring fluorescence spectra of individual airborne particles sampled from ambient air provides the following state of technology information: "Detecting chemical composition of particles is desirable for a variety of applications, such as in detecting fugitive aerosol pollutants, differentiating between biological and non-biological aerosols (and classifying biological particles), or investigating aerosol drug-delivery systems. Light scattering particle counters are based on a single-particle detection approach, wherein particles entrained in air are rapidly drawn through an intense light beam, and light scattered by single particles is sensed and used to infer particle size. Recently, this approach has been expanded to measurement of the two-dimensional angular optical scattering of single aerosol particles and the intrinsic laser-induced fluorescence (LIF) of particles, both of which may be used for additional characterization. LIF can be used in addition to (or instead of) elastic scattering. These efforts concentrate on measurement of the undispersed fluorescence of particles, and consequently only have limited potential for providing information on particle composition. More capable techniques to measure the LIF spectra of single aerosol particles have been recently developed in order to obtain better aerosol classification. In these investigations the emphasis was on detecting biological aerosols using both cw and pulsed laser sources with wavelengths ranging from 263 nm to 488 nm."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a "safe" fluorescent particle for a variety of applications. The particle comprises a non-biological, biodegradable carrier and natural fluorophores encapsulated in the non-biological, biodegradable carrier. In some embodiments the particle is used as a simulant for mimicking the fluorescence properties of microorganisms. However, the particle need not mimic the fluorescent characteristics of a microorganism, rather it can be incorporated into one or more natural fluorophores as a means for fluorescence detection. Single or combinations of fluorophores are encapsulated to produce a desired fluorescent effect such as particles that fluoresce at 370 nm maxima. The particles can therefore be tuned to the excitation wavelength of a fluorescence detector.

One application for these particles is their use in aerosol studies, such as large scale air dispersal to track particulate migration over vast areas, or for urban particle dispersion studies. Currently, researchers performing these studies rely on air dispersion models and gas tracer tests to determine the movement and flow of aerosols in urban environments such as in cities—around and through occupied buildings—because "safe" particles are not available. These particles would provide those safety benefits. Furthermore, these particles could be designed with the appropriate density and perhaps shape of a microorganism to mimic the aerodynamic movement of a microorganism.

An example of aerosol study is described in the article, "An examination of the urban dispersion curves derived from the St. Louis dispersion study" by Akula Venkatram in *Atmospheric Environment* 39 (2005) 3813-3822, which describes a study, "The St. Louis study was conducted over the period 1963-1965. The study consisted of a series of 26 daytime and 16 evening experiments in which fluorescent zinc cadmium sulfide particles were released near ground level at two different locations under a variety of meteorological conditions. During the first year of the experiments, the release was at ground level in a relatively open area in a park located west of the downtown area. In the second year, the tracer was released from the top of a three-story building surrounded by trees and similar buildings. The main downtown area, consisting of buildings with an average height of 40 m, was about 5 km away from both release locations." The disclosure of the article, "An examination of the urban dispersion curves derived from the St. Louis dispersion study" by Akula Venkatram in *Atmospheric Environment* 39 (2005) 3813-3822 is incorporated herein by this reference.

Another example of aerosol study is described in the article, "Use of Salt Lake City URBAN 2000 Field Data to Evaluate the Urban Hazard Prediction Assessment Capability (HPAC) Dispersion Model" by Joseph C. Chang in *JOURNAL OF APPLIED METEOROLOGY* pages 485-501 (2005) which provides background about the study, "The potential impacts of the atmospheric release of chemical, biological, radiological, and nuclear (CBRN) or other hazardous materials are of increasing concern. Hazardous releases can occur due to accidents, such as the release of toxic industrial chemicals in Bhopal, India, in 1984 (e.g., Sharan et al. 1996) and the Chernobyl nuclear power plant disaster in the Ukraine in 1986 (e.g., Puhakka et al. 1990). They can also occur as an unintentional result of military actions, such as the U.S. destruction of rockets with chemical warheads at Khamisiyah, Iraq, after the 1991 Gulf War (Winkenwerder 2002). More recently, terrorist incidents in urban settings, such as the events on 11 Sep. 2001 in New York City, N.Y., and Washington, D.C., and military conflicts dramatically raise concerns for the possibility of mass casualties." The disclosure of the article, "Use of Salt Lake City URBAN 2000 Field Data to Evaluate the Urban Hazard Prediction Assessment Capability (HPAC) Dispersion Model" by Joseph C. Chang in *JOURNAL OF APPLIED METEOROLOGY* pages 485-501 (2005) is incorporated herein by this reference.

The evaluation of different biofluorescence detectors as tools to detect biological attack is currently difficult and balkanized due to the lack of a single, common standard with which to compare the different instruments. Biological organisms present substantial drawbacks in that they are difficult to transport and aerosolize without damaging them, exposure to them may present a health risk, and they have a tendency to agglomerate which makes their aerosolization difficult to perform reliably. Furthermore, they have a short shelf life, they are not conveniently disposable, their use requires extensive training, any equipment exposed to them requires bleach or other bactericides/sporicides for cleaning, they are difficult to manufacture, and many aspects of their growth and handling affect their final state. Therefore, biological organisms are not optimal evaluation, calibration, and training standards for biofluorescence instruments. They are, however, fluorescent in the precise manner of a microorganism (obviously), which is ultimately necessary for a test agent or surrogate.

The present invention provides a simulant for mimicking the fluorescence properties of microorganisms. The simulant comprises a non-biological carrier and natural fluorophores encapsulated in the non-biological carrier. By doping biodegradable-polymer drug delivery microspheres with natural or synthetic fluorophores, the fluorescence of biological organisms can be simulated without the associated risks and logistical difficulties associated with handling live microorganisms. The particles can be "tuned" to exhibit the fluorescence characteristics of any microorganism by changing the fluorophore ratios. Because the particles are both inert and biodegradable, and because the natural fluorophores are not harmful to humans, there would be no risks to human exposure in the course of training, evaluating or tuning, and calibrating conventional fluorescence bioaerosol particle sensors.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

FIG. 1 illustrates one embodiment of a system constructed in accordance with the present invention.

FIG. 2 illustrates another embodiment of a system constructed in accordance with the present invention.

FIG. 3 illustrates yet another embodiment of a system constructed in accordance with the present invention.

FIG. 4 is an illustration showing that the naturally occurring fluorophores are chosen to match the spectral characteristics of the microorganism that is to be detected.

FIG. 5 illustrates one embodiment of a system for producing simulants to mimic the fluorescence properties of microorganisms.

FIG. 6 illustrates another embodiment of a system for producing simulants to mimic the fluorescence properties of microorganisms.

FIG. 7 illustrates another embodiment of a system constructed in accordance with the present invention.

DETAILED DESCRIPTION OF THE INVENTION

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

The January/February 2002 issue of Science & Technology Review, in an article titled "Rapid Field Detection of Biological Agents," describes two systems to rapidly detect and identify biological agents, including pathogens such as anthrax and plague. The systems are the Handheld Advanced Nucleic Acid Analyzer (HANAA) and the Autonomous Pathogen Detection System (APDS). About the size of a brick, the HANAA biodetection system can be held in one hand and weighs less than a kilogram. The system was designed for emergency response groups, such as firefighters and police, who are often first on the scene at sites where bioterrorism may have occurred. Each handheld system can test four samples at once—either the same test on four different samples or four different tests on the same sample. HANAA can provide results in less than 30 minutes, compared with the hours to days that regular laboratory tests typically take. To detect the DNA in a sample, a synthesized DNA probe tagged with a fluorescent dye is introduced into the sample before it is inserted into the heater chamber. Each probe is designed to attach to a specific organism, such as anthrax or plague. Thus, the operator must have an idea of what substances might be involved. "The system doesn't test for all unknowns," says Langlois. "A responder has to decide what kinds of pathogens to test for ahead of time and set up the system accordingly." If that organism is present in the sample, the probe attaches to its DNA, which is then amplified during the PCR process, releasing the fluorescent tag. HANAA measures the sample's fluorescence and the presence (or absence) of the targeted organism. Whereas HANAA can be hand-carried to sites at which an attack is suspected to have happened, the APDS is stationed in one place for continuous monitoring and is designed to work much like a smoke detector, but for pathogens. When fully developed, the APDS could be placed in a large area such as an airport, a stadium, or a conference hall. The system will sample the air around the clock and sound an alarm if pathogens are detected. The disclosure of the article titled "Rapid Field Detection of Biological Agents," in the January/February 2002 issue of Science & Technology Review is incorporated herein by this reference.

The October 2004 issue of Science & Technology Review, in an article titled "Detecting Bioaerosols When Time is of the Essence," states that Livermore researchers received seed funding from the Laboratory Directed Research and Development Program to develop an instrument that counters bioterrorism by providing a rapid early warning system for pathogens, such as anthrax. That instrument, the Autonomous Pathogen Detection System (APDS), is now ready for deployment to better protect the public from a bioaerosol attack, and the development team has been honored with a 2004 R&D 100 Award. In September 2003, APDS passed a series of pathogen exposure tests at a high-containment laboratory at the Dugway Proving Ground in Utah. In these trials, the system clearly demonstrated that it could detect real pathogens and confirm the identifications with a fully automated second assay method. APDS units were also deployed at the Albuquerque Airport in New Mexico and at a Washington, D.C., Metro station, where they provided continuous monitoring for up to seven days, unattended. The system can be adapted for situations where environmental or clinical pathogens require monitoring. For example, APDS could test for mold or fungal spores in buildings or for the airborne spread of contagious materials in hospitals. It also could identify disease outbreaks in livestock transport centers or feedlots. The disclosure of the article titled "Detecting Bioaerosols When Time is of the Essence," in the October 2004 issue of Science & Technology Review is incorporated herein by this reference.

The evaluation of different biofluorescence detectors as tools to detect biological attack is currently difficult and balkanized due to the lack of a single, common standard with which to compare the different instruments. Biological organisms present substantial drawbacks in that they are difficult to transport and aerosolize without damaging them, exposure to them presents a health risk, and they have a tendency to agglomerate which makes their aerosolization difficult to perform reliably. Furthermore, they have a short shelf life, they are not conveniently disposable, their use requires extensive training, any equipment exposed to them requires bleach or other bactericides/sporicides for cleaning, they are difficult to manufacture, and many aspects of their growth and handling affect their final state. Therefore, biological organisms are not optimal evaluation, calibration, and training standards for biofluorescence instruments. They are, however, fluorescent in the precise manner of a microorganism (obviously), which is ultimately necessary for a test agent or surrogate.

Figure 1:
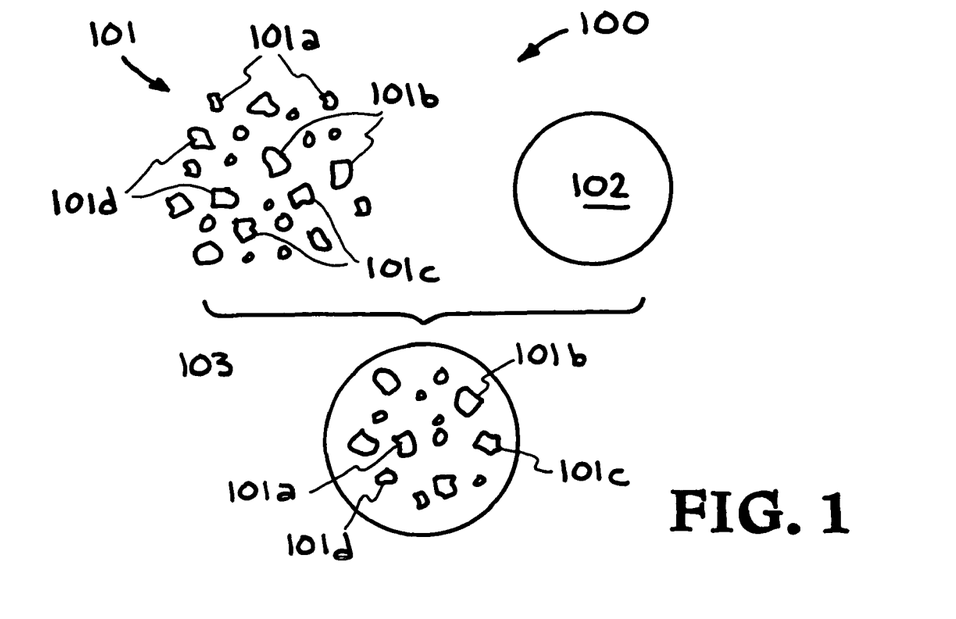

Referring now to the drawings and in particular to FIG. 1, one embodiment of a system constructed in accordance with the present invention is illustrated. The system is designated generally by the reference numeral 100. The system 100 provides encapsulation of natural fluorophores in non-toxic, abiotic materials as a simulant to mimic the fluorescence properties of microorganisms.

As illustrated in FIG. 1, naturally occurring fluorophores 101 are combined with a non-biological carrier 102 to produce a simulant 103 that mimics the fluorescence properties of microorganisms. The system 100 provides the simulant 103 that is used for field aerosol studies, mock biowarfare training, training for rapid assessment of bioweapons labs, calibrating fluorescence-based detection equipment, and other uses.

The naturally occurring fluorophores 101 are chosen to match the spectral characteristics of the microorganism that is to be detected. The naturally occurring fluorophores 101 include different fluorophores with different spectral characteristics. As illustrated in FIG. 1 the fluorophores 101 comprise fluorophores 101A, 101B, 101C, 101D, etc. The make up of the fluorophores 101 are chosen so that the ratio of the fluorophores 101A, 101B, 101C, 101D, etc. matches the spectral characteristics of a preselected microorganism. By altering the fluorophore ratios, the spectral characteristics of any microorganism can be matched. The simulant 103 that is produced includes the fluorophores 101A, 101B, 101C, 101D, etc. that have a ratio of fluorescence that matches the spectral characteristics of a microorganism that has been preselected for testing. The simulant 103 provides a microsphere that can be "tuned" to exhibit the fluorescence characteristics of threat agents.

The non-biological carrier 102 is made of non-toxic materials. In one embodiment the non-biological carrier 102 is made of abiotic materials. In another embodiment the non-biological carrier 102 is made of a biodegradable polymer. The non-biological carrier 102 illustrated in FIG. 1 is made of a biodegradable polymer that is approved by the U.S. Food and Drug Administration (US-FDA) for in vivo research. The biodegradable polymer used as the non-biological carrier 102 is a polymer of lactic and/or glycolic acids such as poly (lactide-co-glycolide) (PLGA). The non-biological carrier 102 has advantages because it is US-FDA approved, is safe for humans, is used for drug delivery, is directed to localized regions in the body by injection, is digested/destroyed by the natural immune response, and has sustained-release properties.

The simulant 103 is a biodegradable polymer microsphere. Biodegradable polymer microspheres are currently used in the pharmaceutical field for in vivo drug delivery. Some of the advantages of using microspheres in therapeutics are: (1) they are safe for humans, (2) they can target localized regions by injection or functionalization, (3) they may be used for sustained release delivery of chemo and hormone therapeutic regimens, and (4) they are digested by macrophages and dendritic cells.

The simulant 103 is a biodegradable polymer microsphere that can be "tuned" to exhibit the fluorescence characteristics of threat agents. Most of the fluorescence in biological organisms comes from natural fluorophores such as the aromatic amino acids; tryptophan, phenylalanine, and tyrosine; NADH, picolinic acid, and flavins. These microspheres combine the fluorescence characteristics of the microorganisms, the handling characteristics of the polystyrene latex microspheres, and the safety characteristics of the biodegradable polymer microspheres. If these natural fluorophores are doped into biodegradable polymer microspheres in the correct ratios, then those spheres will act as fluorescent analogs to microorganisms. Furthermore, by varying the concentrations of the various fluorophores, different agents can be simulated. If inhaled or ingested, the natural fluorophore-doped biodegradable polymer particles would be digested by the human macrophages and so are not detrimental to human health. The doped biodegradable polymers have the combined advantages of the fluorescence characteristics of the microorganisms, the handling characteristics of the polystyrene latex microspheres and the safety characteristics of the biodegradable polymer microspheres.

The system 100 combines the advantages of natural fluorophores, common to both humans and microorganisms, with the safety benefits of a biodegradable polymer. The system 100 has advantages because it has properties conducive to field operations/tests including (1) it is easily used by untrained personnel, (2) it is stable in most environments, (3) it has long shelf-life, (4) it is stable at pH>3, and (5) it may have increased hydrophobicity=stability in wetter conditions. Degradation studies indicate:

Lyophilized lactide and/or glycolide microspheres (50:50 polymer ratio) stable for >3 months when stored at 4° C. or frozen, stable during testing and calibration procedures at elevated temperatures (>37° C. for 6 days), have the precision of an analytical reagent, labeled (fluorescent tag) to differentiate between test simulants and threat agents, and surface properties can be altered by functionalization/derivatization, hydrophobicity, surface charge, surface proteins/antigens for special applications.

The system 100 enables the mimicking of the fluorescence signatures of threat agents and the development of a field-deployable simulant 103. The system 100 provides simulant 103 that can be used for field aerosol studies, mock biowarfare training, training for rapid assessment of bioweapons labs, calibrating fluorescence-based detection equipment, and other uses. The system 100 can also be use in other applications, for example the system 100 can be used to provide a simulant for air dispersion studies (large scale); for urban aerosol studies (small scale); for tagging, tracking, and locating; and for subsurface colloidal transport studies/radionuclide migration studies. The system 100 can be used to simulate the fluorescent properties of microorganisms. Size can be adjusted to simulate different degrees of agglomeration. The system 100 can be used as challenge-test standards for determining sensitivity and specificity of fluorescent detection technologies. The system 100 can be used for large-scale air current deployments or tests for determining the movement and distribution of particles in urban environments. The system 100 can be labeled to distinguish between "test" microspheres and background microorganisms/organic particles. The system 100 can be used as a calibration standard for bio-fluorescence detectors. The system 100 can be used to train personnel to operate bio-fluorescence detectors. Surface properties, such as hydrophobicity and surface charge, can be tuned/altered for various applications.

Figure 2:
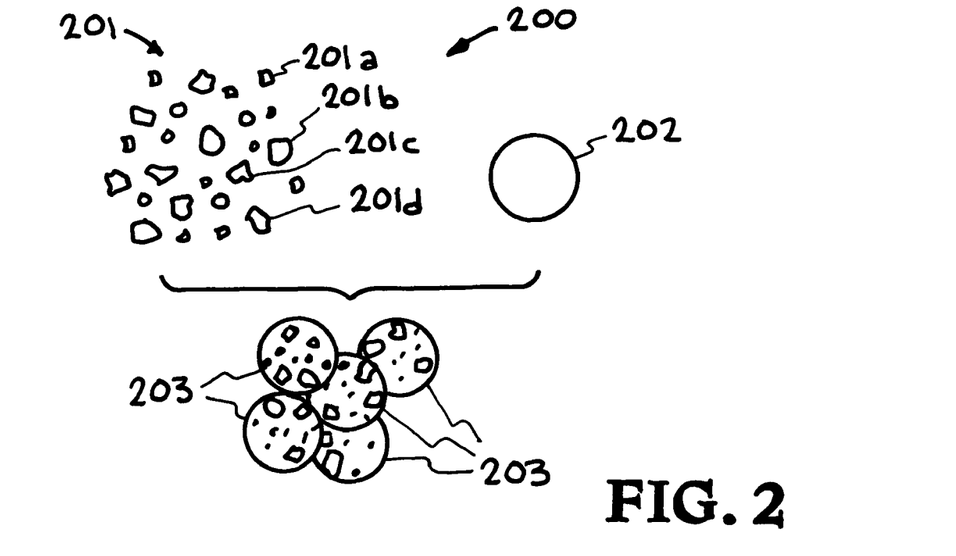

Referring now to FIG. 2, another embodiment of a system constructed in accordance with the present invention is illustrated. The system is designated generally by the reference numeral 200. The system 200 provides encapsulation of natural fluorophores 201 in non-toxic, abiotic materials 202 to provide simulants 203 that mimic the fluorescence properties of microorganisms.

The simulants 203 are biodegradable polymer microspheres. The biodegradable polymer microsphere simulants 203 can be "tuned" to exhibit the fluorescence characteristics of threat agents. Most of the fluorescence in biological organisms comes from natural fluorophores such as the aromatic amino acids; tryptophan, phenylalanine, and tyrosine; NADH, picolinic acid, and flavins. These microspheres combine the fluorescence characteristics of the microorganisms, the handling characteristics of the polystyrene latex microspheres, and the safety characteristics of the biodegradable polymer microspheres. If these natural fluorophores are doped into biodegradable polymer microspheres in the correct ratios, then those spheres will act as fluorescent analogs to microorganisms. By varying the concentrations of the various fluorophores, different agents can be simulated.

As illustrated in FIG. 2, naturally occurring fluorophores 201 are combined with non-biological carriers 202 to produce simulants 203 that mimic the fluorescence properties of microorganisms. The system 200 provides simulants 203 that are useful for field aerosol studies, mock biowarfare training, training for rapid assessment of bioweapons labs, calibrating fluorescence-based detection equipment, and other uses.

The naturally occurring fluorophores 201 include different fluorophores with different spectral characteristics. As illustrated in FIG. 2 the fluorophores 201 comprise fluorophores 201A, 201B, 201C, 201D, etc. The make up of the fluorophores 201 are chosen so that the ratio of the fluorophores 201A, 201B, 201C, 201D, etc. matches the spectral characteristics of a preselected microorganism. By altering the fluorophore ratios, the spectral characteristics of any microorganism can be matched. The simulants 203 that are produced include the fluorophores 201A, 201B, 201C, 201D, etc. that have a ratio of fluorescence that matches the spectral characteristics of a microorganism that has been preselected for testing. The simulants 203 are microspheres that can be "tuned" to exhibit the fluorescence characteristics of threat agents.

The non-biological carrier 202 is made of non-toxic materials. In one embodiment the non-biological carrier 202 is made of abiotic materials. In another embodiment the non-biological carrier 202 is made of a biodegradable polymer. The non-biological carrier 202 illustrated in FIG. 2 is made of a biodegradable polymer that is approved by the U.S. Food and Drug Administration (US-FDA) for in vivo research. The biodegradable polymer used as the non-biological carrier 202 is a polymer of lactic and/or glycolic acids such as poly (lactide-co-glycolide) (PLGA). The non-biological carrier 202 has advantages because it is US-FDA approved, is safe for humans, is used for drug delivery, is directed to localized regions in the body by injection, is digested/destroyed by the natural immune response, and has sustained-release properties.

The system 200 combines the advantages of natural fluorophores, common to both humans and microorganisms, with the safety benefits of a biodegradable polymer. The system 200 has advantages because it has properties conducive to field operations/tests including (1) it is easily used by untrained personnel, (2) it is stable in most environments, (3) it has long shelf-life, (4) it is stable at pH>3, and (5) it can be designed to have increased hydrophobicity=stability in wetter conditions. Degradation studies indicate:

Lyophilized PLGA microspheres (50:50 polymer ratio) are stable for >3 months when stored at 4° C. or frozen, and stable during testing and calibration procedures at elevated temperatures (>37° C. for 6 days). Furthermore, they can be used with the precision of an analytical reagent, labeled (fluorescent tag) to differentiate between test simulants and threat agents, their surface properties can be altered by functionalization/derivatization to alter surface charge or attach surface proteins/antigens for special applications.

The system 200 enables the mimicking of the fluorescence signatures of threat agents and the development of field-deployable simulants 203. The system 200 provides simulants 203 that can be used for field aerosol studies, mock biowarfare training, training for rapid assessment of bioweapons labs, calibrating fluorescence-based detection equipment, and other uses. The system 200 can also be use in other applications, for example the system 200 can be used for to provide simulants for air dispersion studies (large scale); for urban aerosol studies (small scale); for tagging, tracking, and locating; and for subsurface colloidal transport studies/radionuclide migration studies. The system 200 can be used to simulate the fluorescent properties of microorganisms. Size can be adjusted to simulate different degrees of agglomeration. The system 200 can be used as challenge-test standards for determining sensitivity and specificity of fluorescent detection technologies. The system 200 can be used for large-scale air current deployments or tests for determining the movement and distribution of particles in urban environments. The system 200 can be labeled to distinguish between "test" microspheres and background microorganisms/organic particles. The system 200 can be used as a calibration standard for bio-fluorescence detectors. The system 200 can be used to train personnel to operate bio-fluorescence detectors. Surface properties, such as hydrophobicity and surface charge, can be tuned/altered for various applications.

Figure 3:
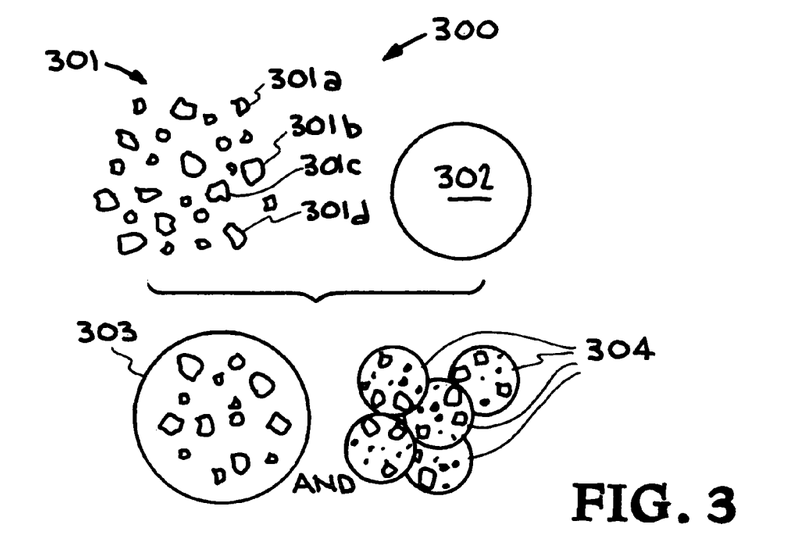

Referring now to FIG. 3, yet another embodiment of a system constructed in accordance with the present invention is illustrated. The system is designated generally by the reference numeral 300. The system 300 provides encapsulation of natural fluorophores 301 in non-toxic, abiotic materials 302 to provide simulants 303 and 304 that mimic the fluorescence properties of microorganisms.

As illustrated in FIG. 3, naturally occurring fluorophores 301 are combined with non-biological carriers 302 to produce simulants 303 and 304 that mimic the fluorescence properties of microorganisms. The system 300 provides simulants 303 and 304 that are useful for field aerosol studies, mock biowarfare training, training for rapid assessment of bioweapons labs, calibrating fluorescence-based detection equipment, and other uses.

The naturally occurring fluorophores 301 include different fluorophores with different spectral characteristics. As illustrated in FIG. 3 the fluorophores 301 comprise fluorophores 301A, 301B, 301C, 301D, etc. The make up of the fluorophores 301 are chosen so that the ratio of the fluorophores 301A, 301B, 301C, 301D, etc. matches the spectral characteristics of a preselected microorganism. By altering the fluorophore ratios, the spectral characteristics of any microorganism can be matched. The simulants 303 and 304 that are produced include the fluorophores 301A, 301B, 301C, 301D, etc. that have a ratio of fluorescence that matches the spectral characteristics of a microorganism that has been preselected for testing. The simulants 303 and 304 are microspheres that can be "tuned" to exhibit the fluorescence characteristics of threat agents.

The non-biological carrier 302 is made of non-toxic materials. In one embodiment the non-biological carrier 302 is made of abiotic materials. In another embodiment the non-biological carrier 302 is made of a biodegradable polymer. The non-biological carrier 302 illustrated in FIG. 3 is made from a biodegradable polymer that is approved by the U.S. Food and Drug Administration (US-FDA) for in vivo research. The biodegradable polymer used as the non-biological carrier 302 is a polymer of lactic and/or glycolic acids such as poly(lactide-co-glycolide) (PLGA). The non-biological carrier 302 has advantages because it is US-FDA approved, is safe for humans, is used for drug delivery, is directed to localized regions in the body by injection, is digested/destroyed by the natural immune response, and has sustained-release properties.

The simulants 303 and 304 are biodegradable polymer microspheres. The biodegradable polymer microsphere simulants 303 and 304 can be "tuned" to exhibit the fluorescence characteristics of threat agents. Most of the fluorescence in biological organisms comes from natural fluorophores such as the aromatic amino acids; tryptophan, phenylalanine, and tyrosine; NADH, picolinic acid, and flavins. These microspheres combine the fluorescence characteristics of the microorganisms, the handling characteristics of the polystyrene latex microspheres, and the safety characteristics of the biodegradable polymer microspheres. If these natural fluorophores are doped into biodegradable polymer microspheres in the correct ratios, then those spheres will act as fluorescent analogs to microorganisms. By varying the concentrations of the various fluorophores, different agents can be simulated.

The system 300 combines the advantages of natural fluorophores, common to both humans and microorganisms, with the safety benefits of a biodegradable polymer. The system 300 has advantages because it has properties conducive to field operations/tests including (1) is easily used by untrained personnel, (2) it is stable in most environments, (3) it has long shelf-life, (4) it is stable at pH>3, and (5) it can be designed to have increased hydrophobicity=stability in wetter conditions. Degradation studies indicate that:

Lyophilized PLGA microspheres (50:50 polymer ratio) are stable for >3 months when stored at 4° C. or frozen, and stable during testing and calibration procedures at elevated temperatures (>37° C. for 6 days). Furthermore, they can be used with the precision of an analytical reagent, can be labeled (fluorescent tag) to differentiate between test simulants and threat agents, their surface properties can be altered by functionalization/derivatization to alter surface charge or attach surface proteins/antigens for special applications.

The system 300 enables the mimicking of the fluorescence signatures of threat agents and the development of field-deployable simulants 303 and 304. The system 300 provides simulants 303 and 304 that can be used for field aerosol studies, mock biowarfare training, training for rapid assessment of bioweapons labs, calibrating fluorescence-based detection equipment, and other uses. The system 300 can also be use in other applications, for example the system 300 can be used for to provide simulants for air dispersion studies (large scale); for urban aerosol studies (small scale); for tagging, tracking, and locating; and for subsurface colloidal transport studies/radionuclide migration studies. The system 300 can be used to simulate the fluorescent properties of microorganisms. Size can be adjusted to simulate different degrees of agglomeration. The system 300 can be used as challenge-test standards for determining sensitivity and specificity of fluorescent detection technologies. The system 300 can be used for large-scale air current deployments or tests for determining the movement and distribution of particles in urban environments. The system 300 can be labeled to distinguish between "test" microspheres and background microorganisms/organic particles. The system 300 can be used as a calibration standard for bio-fluorescence detectors. The system 300 can be used to train personnel to operate bio-fluorescence detectors. Surface properties, such as hydrophobicity and surface charge, can be tuned/altered for various applications.

Figure 4:
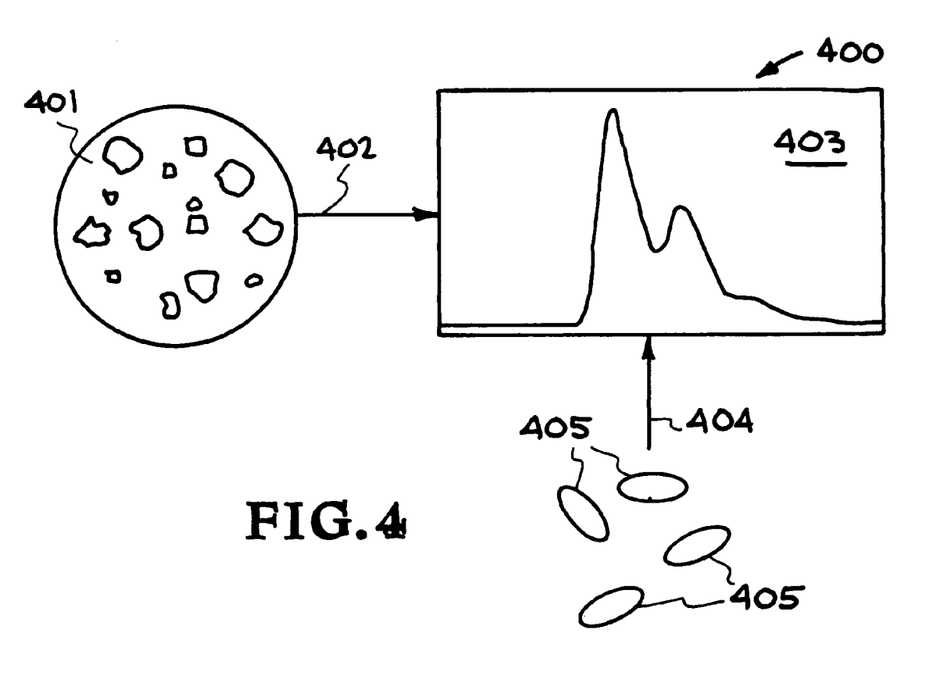

Referring now to FIG. 4, an illustration shows that the naturally occurring fluorophores of the simulant are chosen to match the spectral characteristics of the microorganism that is to be detected. The illustration is designated generally by the reference numeral 400.

A display 403 represents spectral characteristics of naturally occurring fluorophores in the simulant 401 and the spectral characteristics of the microorganism of interest 405. The spectral characteristics of the simulant 401 are represented by the display 403 as illustrated by the arrow 402. The spectral characteristics the microorganism of interest 405 is represented by the display 403 as illustrated by the arrow 404.

The simulant 401 includes different fluorophores with different spectral characteristics. The make up of the fluorophores of the simulant 401 are chosen so that the ratio of the fluorophores matches the spectral characteristics of the preselected microorganism 405. The fluorescence spectrum of simulant 401 matches spectrum of the target microorganism 405. In the illustration 400 the preselected microorganism 405 is *B. anthracis* spore. The simulant 401 and *B. anthracis* spore 405 exhibit the same spectra.

Most of the fluorescence in biological organisms comes from natural fluorophores such as the aromatic amino acids, tryptophan, tyrosine and phenylalanine, and NADH, dipicolinic acid and flavins. These microspheres combine the fluorescence characteristics of the microorganisms, the handling characteristics of the polystyrene latex microspheres, and the safety characteristics of the biodegradable polymer microspheres. If these natural fluorophores are doped into biodegradable polymer microspheres in the correct ratios, then those spheres will act as fluorescent analogs to microorganisms. Furthermore, by varying the concentrations of the various fluorophores, different agents can be simulated. The simulant 401 is a biodegradable polymer microsphere that can be "tuned" to exhibit the fluorescence characteristics of threat agents.

By altering the fluorophore ratios of the simulant 401, the spectral characteristics of any microorganism can be matched. The simulant 401 includes a mixture of fluorophores that match the spectral characteristics of the microorganism 405 that has been preselected for testing. The simulant 401 provides a microsphere that can be "tuned" to exhibit the fluorescence characteristics of threat agents.

The present invention enables the mimicking of the fluorescence signatures of threat agents and the development of a field-deployable simulant 401. The simulant 401 can be used for field aerosol studies, mock biowarfare training, training for rapid assessment of bioweapons labs, calibrating fluorescence-based detection equipment, and other uses. The simulant 401 can also be use in other applications, for example the simulant 401 can be used to provide a fluorescence simulant for air dispersion studies (large scale); for urban aerosol studies (small scale); for tagging, tracking, and locating; and for a subsurface colloidal transport studies/radionuclide migration studies. The simulant 401 can be used to simulate the fluorescent properties of microorganisms. Size can be adjusted to simulate different degrees of agglomeration. The simulant 401 can be used as challenge-test standards for determining sensitivity and specificity of fluorescent detection technologies. The simulant 401 can be used for large-scale air current deployments or tests for determining the movement and distribution of particles in urban environments. The simulant 401 can be labeled to distinguish between "test" microspheres and background microorganisms/organic particles. The simulant 401 can be used as a calibration standard for bio-fluorescence detectors. The simulant 401 can be used to train personnel in identifying bio-threat agents with fluorescence detection technologies. Surface properties, such as hydrophobicity and surface charge, can be tuned/altered for various applications.

Figure 5:
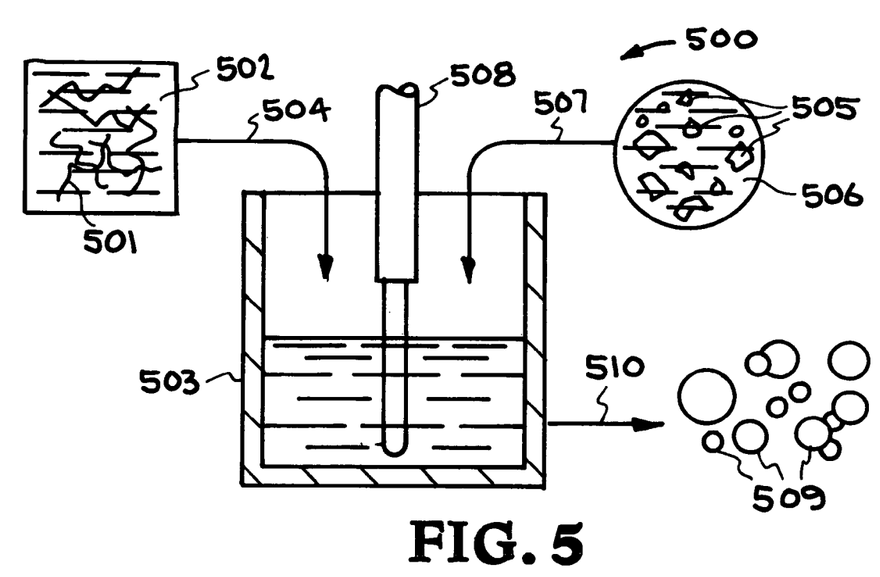

Referring now to the drawings and in particular to FIG. 5, one embodiment of a system for producing simulants to mimic the fluorescence properties of microorganisms constructed in accordance with the present invention is illustrated. The system is designated generally by the reference numeral 500. The system 500 is an oil-in-water emulsion system. The system 500 provides a system for producing natural fluorophores in non-toxic, abiotic materials that can be used as a simulants to mimic the fluorescence properties of microorganisms.

As illustrated in FIG. 5, biodegradable polymers 501 in solvent 502 are introduced into a container 503 as illustrated by the arrow 504. Also natural fluorophores 505 in water 506 are introduced into the container 503 as illustrated by the arrow 507. The biodegradable polymers 501 in solvent 502 and natural fluorophores 505 in water 506 are mixed in container 503 by mixing system 508 to produce polydisperse microspheres 509 as illustrated by the arrow 510.

The polydisperse microspheres 509 contain the naturally occurring fluorophores 505. This provides a simulant that mimics the fluorescence properties of microorganisms. The polydisperse microspheres simulant 509 can be used for field aerosol studies, mock biowarfare training, training for rapid assessment of bioweapons labs, calibrating fluorescence-based detection equipment, and other uses.

The naturally occurring fluorophores 505 are chosen to match the spectral characteristics of the microorganism that is to be detected. The naturally occurring fluorophores 505 include different fluorophores with different spectral characteristics. The make up of the fluorophores 505 are chosen so that the ratio of the fluorophores match the spectral characteristics of a preselected microorganism. By altering the fluorophore ratios, the spectral characteristics of any microorganism can be matched.

The oil-in-water emulsion system 500 utilizes a simple water-in-oil emulsion. Fluorophores 505 are dissolved in water 506. Polymer 501 is dissolved in solvent 502. The next step is to disperse aqueous phase in polymer solution with ultrasonic probe 508. Particle size distribution is dependent on the degree of ultrasonication. The solvent is subsequently evaporated or spray-dried and the microspheres are washed and dried under vacuum.

Figure 6:
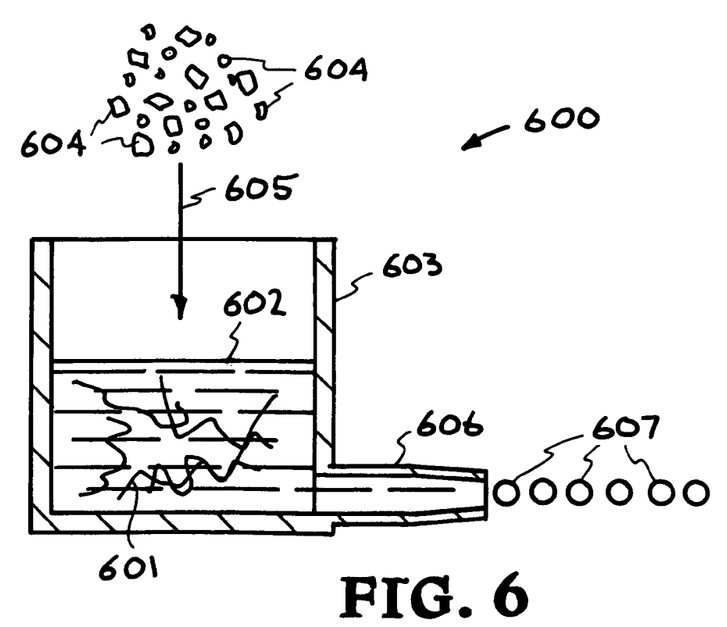

Referring now to the drawings and in particular to FIG. 6, another embodiment of a system for producing simulants to mimic the fluorescence properties of microorganisms constructed in accordance with the present invention is illustrated. The system is designated generally by the reference numeral 600. The system 600 is a pulsed/jetted system. The system 600 provides a system for producing natural fluorophores in non-toxic, abiotic materials that can be used as a simulants to mimic the fluorescence properties of microorganisms.

As illustrated in FIG. 6, biodegradable polymers 601 in a solvent 602 are contained in container 603. Natural fluorophores 604 are introduced into the container 603 as illustrated by the arrow 605. The biodegradable polymers 601 and natural fluorophores 604 mix in container 603. Monodisperse microspheres 607 of a desired size can be produced directly from the fluorophore/polymer dispersion by using a vibrating orifice aerosol generator, ink jet aerosol generator, or other particle generator 606 with subsequent drying to remove the solvent. A VOAG, ink jet particle generator, or other particle generator 606 is used to produce the monodisperse microspheres 607.

The monodisperse microspheres 607 contain the naturally occurring fluorophores 604. This provides simulants that mimic the fluorescence properties of microorganisms. The monodisperse microspheres simulants 607 can be used for field aerosol studies, mock biowarfare training, training for rapid assessment of bioweapons labs, calibrating fluorescence-based detection equipment, and other uses.

The naturally occurring fluorophores 604 are chosen to match the spectral characteristics of the microorganism that is to be detected. The naturally occurring fluorophores 604 include different fluorophores with different spectral characteristics. The make up of the fluorophores 604 are chosen so that the ratio of the fluorophores match the spectral characteristics of a preselected microorganism. By altering the fluorophore ratios, the spectral characteristics of any microorganism can be matched.

Figure 7:
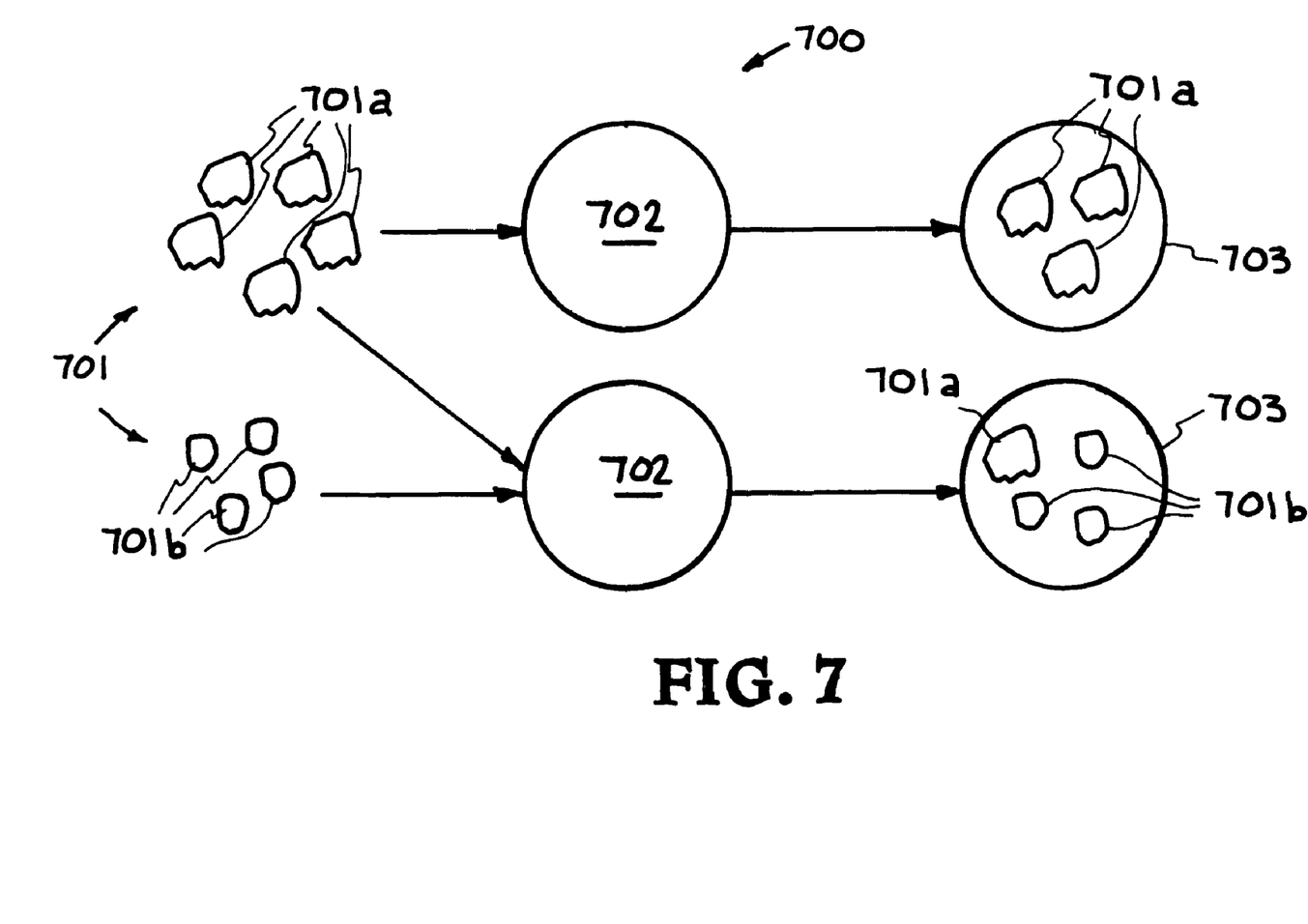

FIG. 7 illustrates the encapsulation of natural fluorophores in non-toxic, abiotic materials as a safe test particle. This system is designated generally by the reference number 700.

The naturally occurring fluorophores 701 include different fluorophores with different spectral characteristics. As illustrated in FIG. 7 the fluorophores 701 comprise fluorophores 701A, 701B, etc.

The non-biological carrier 702 is made of non-toxic materials. In one embodiment the non-biological carrier 702 is made of abiotic materials. In another embodiment the non-biological carrier 702 is made of a biodegradable polymer. The non-biological carrier 702 illustrated in FIG. 7 is made of a biodegradable polymer that is approved by the U.S. Food and Drug Administration (US-FDA) for in vivo research. The biodegradable polymer used as the non-biological carrier 702 is a polymer of lactic and/or glycolic acids such as poly (lactide-co-glycolide) (PLGA). The non-biological carrier 702 has advantages because it is US-FDA approved, is safe for humans, is used for drug delivery, is directed to localized regions in the body by injection, is digested/destroyed by the natural immune response, and has sustained-release properties.

The particle 703 that is produced includes the fluorophores in different concentrations or ratios for a desired effect. The simulant 703 provides a microsphere that can be "tuned" to exhibit the desired fluorescence characteristics.

The simulant 703 is a safe biodegradable polymer microsphere that can be "tuned" to exhibit the desired fluorescence effect. Most of the fluorescence in biological organisms comes from natural fluorophores such as the aromatic amino acids; tryptophan, phenylalanine, and tyrosine; NADH, picolinic acid, and flavins. These microspheres combine natural fluorophores with the safety characteristics of the biodegradable polymer. By varying the concentrations and ratios of the natural fluorophores, different fluorescent effects can be expressed. If inhaled or ingested, the natural fluorophore-doped biodegradable polymer particles would be digested by the human macrophages and so are not detrimental to human health. The doped biodegradable polymers have the combined advantages of using natural fluorophores, the safety characteristics of the biodegradable polymer, and the handling characteristics of the polystyrene latex microspheres.

The simulant 703 can be used in many applications, for example the simulant 703 can be used to provide a fluorescence simulant for fluorescence detection instruments used in air dispersion studies (large scale), urban aerosol studies (small scale), tagging, tracking, and locating, and for subsurface colloidal transport studies/radionuclide migration studies.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A method of making a simulant of a microorganism to be detected for triggering, testing or calibrating aerosol systems wherein the microorganism to be detected has spectral characteristics, comprising the steps of:
preparing a fluorescent particle that mimics the fluorescence properties of the microorganism to be detected by providing a non-biological carrier, and
encapsulating natural occurring fluorophores in said non-biological carrier to produce the simulant for testing or calibrating the aerosol systems, wherein said natural occurring fluorophores including different fluorophores with different spectral characteristics that combine to match the spectral characteristics of the microorganism to be detected.

2. The method of making a simulant of claim 1 wherein said step of providing a non-biological carrier comprises producing said non-biological carrier from abiotic materials.

3. The method of making a simulant of claim 1 wherein said step of providing a non-biological carrier comprises producing said non-biological carrier from a biodegradable polymer.

4. The method of making a simulant of a microorganism to be detected of claim 1 wherein said step of encapsulating natural occurring fluorophores in said non-biological carrier comprises encapsulating at least three different fluorophores with different spectral characteristics in said non-biological carrier and wherein said different spectral characteristics of said at least three different fluorophores match the spectral characteristics of the microorganism to be detected.

5. The method of making a simulant of a microorganism to be detected of claim 1 wherein said step of encapsulating natural occurring fluorophores in said non-biological carrier comprises encapsulating different fluorophores with different spectral characteristics in said non-biological carrier wherein the ratio of said different spectral characteristics of said different fluorophores with different spectral characteristics matches the spectral characteristics of the microorganism to be detected.

6. The method of making a simulant of claim 1 wherein said steps of providing a non-biological carrier and encapsulating natural occurring fluorophores in said non-biological carrier comprises mixing biodegradable polymers in solvent and natural occurring fluorophores in water to produce polydisperse microspheres with naturally occurring fluorophores.

7. The method of making a simulant of claim 1 wherein said steps of providing a non-biological carrier and encapsulating natural occurring fluorophores in said non-biological carrier comprises mixing biodegradable polymers and natural occurring fluorophores to produce monodisperse microspheres with naturally occurring fluorophores.

8. A method of making a simulant for triggering, testing or calibrating systems for detecting microorganisms, wherein the microorganisms to be detected have spectral characteristics, comprising the steps of:
preparing a fluorescent particle that mimics the fluorescence properties of the microorganisms to be detected by providing biodegradable polymers,
providing natural occurring fluorophores including different natural occurring fluorophores with different spectral characteristics, and
mixing said biodegradable polymers and said different natural occurring fluorophores with different spectral characteristics at a ratio wherein said ratio of said different spectral characteristics of said different fluorophores match the spectral characteristics of the microorganisms to be detected to produce the simulant for testing, triggering or calibrating fluorescence detection systems for detecting microorganisms.

9. The method of making a simulant for triggering, testing or calibrating systems for detecting microorganisms of claim 8 wherein said step of providing biodegradable polymers comprises providing biodegradable polymers in solvent, wherein said step of providing natural occurring fluorophores comprises providing natural occurring fluorophores in water, and said step of mixing said biodegradable polymers and said natural occurring fluorophores comprises ultrasonic mixing said biodegradable polymers in solvent and said natural occurring fluorophores in water to produce the simulant for testing or calibrating the systems for detecting the microorganisms.

10. The method of making a simulant for triggering, testing or calibrating systems for detecting microorganisms wherein the microorganisms to be detected have spectral characteristics of claim 8 wherein said step of providing natural fluorophores comprises providing at least three natural occurring fluorophores with different spectral characteristics wherein the ratio of said at least three natural occurring fluorophores with different spectral characteristics matches the spectral characteristics of a the microorganisms to be detected.

11. A method of making a particle for testing or calibrating systems for detecting microorganisms, wherein the microorganism to be detected has spectral characteristics, comprising the steps of:
preparing a fluorescent particle that mimics the fluorescence properties of the microorganism to be detected by providing a non-biological carrier, and
encapsulating natural occurring fluorophores including different natural occurring fluorophores with different spectral characteristics in said non-biological carrier wherein said different natural occurring fluorophores with different spectral characteristics are at a ratio and wherein said ratio matches the spectral characteristics of the microorganism to be detected.

12. The method of making a particle for triggering, testing or calibrating fluorescence detection systems of claim 11 wherein said step of providing a non-biological carrier comprises producing said non-biological carrier from abiotic materials.

13. The method of making a particle for triggering, testing or calibrating fluorescence detection systems of claim 11 wherein said step of providing a non-biological carrier comprises producing said non-biological carrier from a biodegradable polymer.

14. The method of making a particle for triggering, testing or calibrating fluorescence detection systems of claim 11 wherein said step of encapsulating natural occurring fluorophores in said non-biological carrier comprises encapsulating at least three different natural occurring fluorophores with different spectral characteristics in said non-biological carrier wherein said spectral characteristics of said fluorophores provide desired fluorescence effect wherein said at least three different natural occurring fluorophores with different spectral characteristics are at a ratio and wherein said ratio matches the spectral characteristics of the microorganism to be detected.

15. The method of claim 11 wherein said step of encapsulating natural occurring fluorophores in said non-biological carrier comprises encapsulating at least four different fluorophores with different spectral characteristics in said non-biological carrier wherein the ratio of said different spectral characteristics of said at least four different fluorophores and wherein said ratio matches the spectral characteristics of the microorganism to be detected.

16. The method of making a particle for triggering, testing or calibrating fluorescence detection systems of claim 11 wherein said steps of providing a non-biological carrier and encapsulating natural occurring fluorophores in said non-biological carrier comprises mixing biodegradable polymers in solvent and natural occurring fluorophores in water to produce polydisperse microspheres with naturally occurring fluorophores.

17. The method of making a particle for triggering, testing or calibrating fluorescence detection systems of claim 11 wherein said steps of providing a non-biological carrier and encapsulating natural occurring fluorophores in said non-biological carrier comprises mixing biodegradable polymers and natural occurring fluorophores to produce monodisperse microspheres with naturally occurring fluorophores.

* * * * *